(12) United States Patent
Gono et al.

(10) Patent No.: US 8,093,548 B2
(45) Date of Patent: Jan. 10, 2012

(54) CALIBRATION METHODS FOR BLOOD CONTENT SENSORS

(75) Inventors: Kazuhiro Gono, Sagamihara (JP); Takeshi Suga, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 112 days.

(21) Appl. No.: 12/171,505

(22) Filed: Jul. 11, 2008

(65) Prior Publication Data

US 2010/0005850 A1    Jan. 14, 2010

(51) Int. Cl.
*G01D 18/00*    (2006.01)
(52) U.S. Cl. .................................................. 250/252.1
(58) Field of Classification Search ................ 250/252.1
See application file for complete search history.

(56) References Cited

U.S. PATENT DOCUMENTS

| | | | | |
|---|---|---|---|---|
| 4,998,973 | A * | 3/1991 | Kikuchi | 600/109 |
| 5,365,925 | A * | 11/1994 | Lee | 600/477 |
| 6,516,209 | B2 * | 2/2003 | Cheng et al. | 600/323 |
| 6,876,448 | B2 * | 4/2005 | Imura et al. | 356/326 |
| 2005/0033276 | A1 * | 2/2005 | Adachi | 606/32 |

OTHER PUBLICATIONS

A. Katzir, "Biometrical Fiberoptic Sensors," 1988, Optical Society of America, 1988 Technical Digest Series, vol. 2, pp. 4-6.*

* cited by examiner

*Primary Examiner* — Kiho Kim

(57) ABSTRACT

Methods for calibrating blood content sensors used independently or in conjunction with medical instruments such as traditional or capsule type endoscopes.

17 Claims, 10 Drawing Sheets

CALIBRATION METHODS FOR BLOOD CONTENT SENSORS

CROSS REFERENCE TO RELATED APPLICATIONS

This application is related to U.S. patent application Ser. No. 11/937,185 filed on Nov. 8, 2007, entitled "Capsule Blood Detection System and Method."

FIELD OF THE INVENTION

The present invention relates generally to the calibration of blood content detector sensors. More specifically, the invention relates to methods for calibrating blood content detector sensors useable in traditional and capsule-type endoscopes.

BACKGROUND OF THE INVENTION

Scientists have discovered that a detectable increase in the blood content of superficial mucous membrane occurs proximate cancerous and precancerous lesions in the colon relative to the blood content of healthy tissue as described in, for example, R K Wali, H K Roy, Y L Kim, Y Liu, J L Koetsier, D P Kunte, M J Goldberg, V Turzhitsky and V Backman, Increased Microvascular Blood Content is an Early Event in Colon Carcinogenesis, Gut Vol. 54, pp 654-660 (2005), which is incorporated by reference herein. This phenomenon is referred to as early increase in blood supply (EIBS).

Relying on this phenomenon, it is known that it is possible to predict an area of potential abnormality based on early increase in blood supply (EIBS) in the area of abnormality. Further, it has been discovered, that by using a probe applying collimated light to an area of interest, and detecting the amount of absorbed and reflected light it is possible to provide information to a clinician to guide an endoscope to detect a possible abnormality in vivo without an invasive procedure. Such techniques have been described for example in U.S. patent application Ser. No. 11/937,133 filed on Nov. 8, 2007, entitled "Blood Content Detecting Capsule", assigned to the assignee of the present invention, which is incorporated by reference herein.

Typically, optical blood content detection relies on measuring the amount of light reflected from and interacted with the tissue mucosa back into the blood content detector. Because systems rely on measuring the amount of reflected light, the accuracy of the measurements are greatly impacted if the blood content detector and the spectroscope used to analyze the reflected light are not properly calibrated.

Various techniques exist for calibrating endoscopes. However, traditionally such calibration techniques have required the use of a special-purpose light source that emits light at a known wavelength and at a known intensity. Similarly, EIBS calibration techniques have been proposed wherein the intensity of the reflected light is calibrated utilizing a white diffuser panel. Such techniques are described, for example, in M. P. Siegel et al. Applied Optics, Vol. 45, Issue 2, pp. 335-342 (2006), which is incorporated by reference herein.

However, these proposed calibration techniques that are based on white light diffusion fail to address the fact that spectroscopes, used to perform spectral analysis during a blood content measurement are subject to inaccuracies often due to the misalignment of wavelength measurement values for the incident light. Such misalignments may occur due to inconsistent production variations, environmental changes, e.g., temperature and humidity, or variations due to use over time.

Other known techniques that employ wavelength calibration, however, require special-purpose calibration lights at significant costs and are limited to wavelength correction and cannot be utilized for intensity correction. Calibration of optical blood content detectors is further complicated by the fact that blood content detection relies on collecting light reflected from and interacted with the underlying tissue entering the detector at predetermined angles. In particular, it has been found that light reflected at, for example, at around 15 degrees with respect to the surface of living tissue aides in reducing the reflections. Because of this requirement, reliance on a special-purpose light for calibration is difficult because of the inability to ensure that transmitted calibration light is actually entering the blood content detector probe at the desired angle.

Accordingly, a need exists for an improved calibration technique for calibrating a blood content detector without reliance on special-purpose lights or other extraneous equipment in order to maintain a high level or improve the accuracy of blood content detector measurements.

SUMMARY OF THE INVENTION

Systems and methods used for blood content detection and general observation in vivo are advantageously improved if the utilized components and detectors are calibrated prior to use. The need for calibration arises due to the manufacturing differences between equipment, transportation of equipment, environmental factors such as temperature and humidity, as well as many others. The aspects of the present invention provide for accurate and reliable calibration of optical blood content detectors in both the wavelength and intensity ranges without the need for calibrated light sources to acts as standards during the calibration process.

In one embodiment of the present invention, blood content detector calibration relies on a light source disposed within the detector to emit light that is reflected from a calibration reference target at a wavelength range. Suitable calibration reference targets include, for example, white panels and white diffuser panels. The reflected light from the calibration reference target is sensed by the detector for generating calibration coefficients useable in the blood content measurement detection. In addition, the calibration reference target may be used in conjunction with an optical filter to calculate and correct for measurement intensity.

In a second embodiment of the present invention, it is possible to eliminate the optical filter from the above described calibration process if the white diffuser panel or other reference target is replaced by a colored or pigmented reference target that reflects light within the desired wavelength range. The coloration of the reference target may be achieved by, for example, mixing the desired pigment into the reference target itself, or may be achieved by an adhesive film applied to the reference target. It may also be a colored optical element placed on top of a white or other colored reference target.

In a third embodiment of the present invention, the blood content detector may contain separate calibration illuminators that emit light at wavelength spectrums that bracket the desired observation light spectrum, e.g., substantially above and below 500 and 650 nm wavelengths respectively. In such an embodiment, a white panel diffuser is utilized as the reference target such that, in operation, the amount of calibration light is detected to produce calibration or correction coefficients.

BRIEF DESCRIPTION OF THE DRAWINGS

For a better understanding of the present invention, reference is made to the following description and accompanying drawings, while the scope of the invention is set forth in the appended claims:

DETAILED DESCRIPTION

Figure 1:
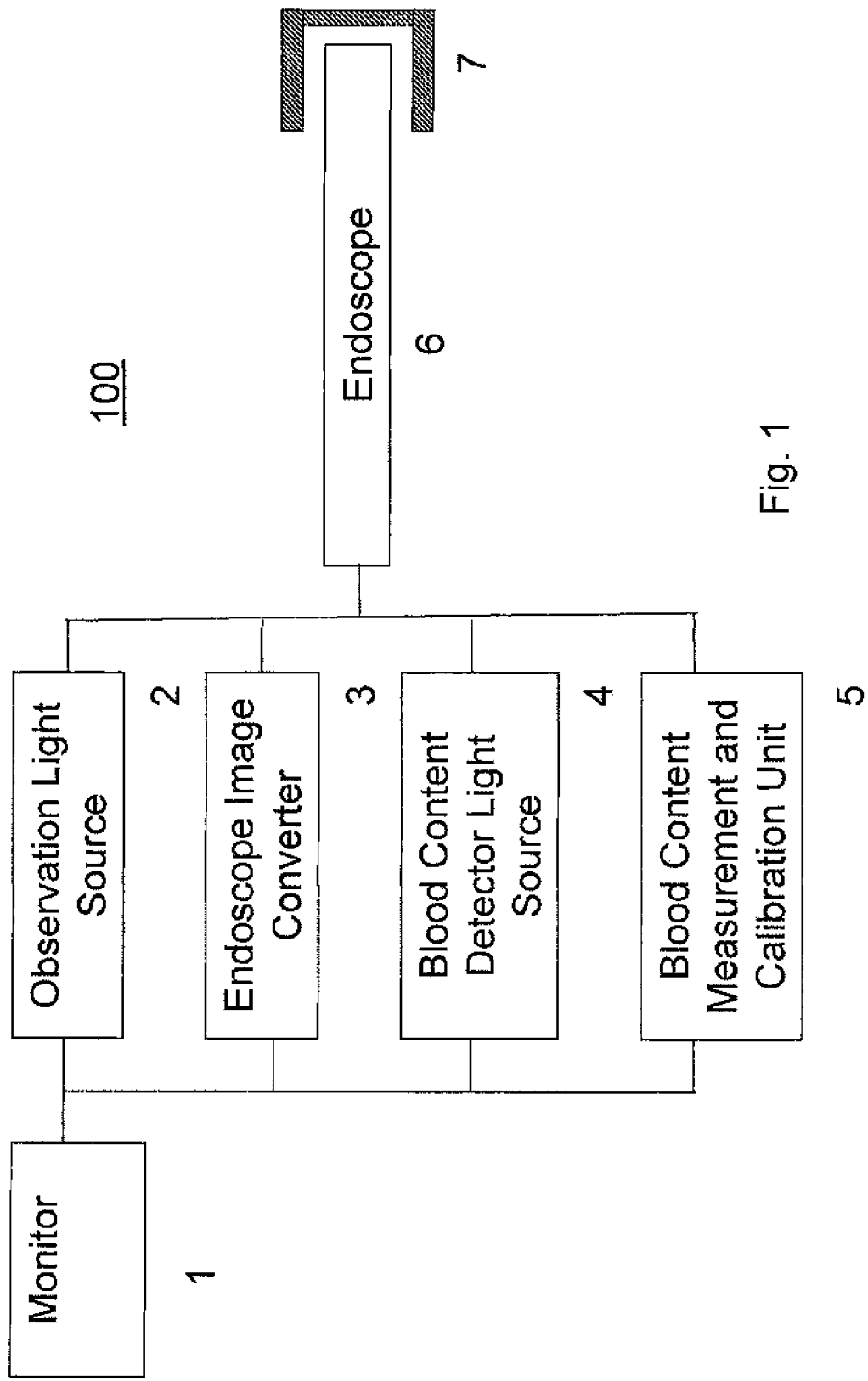
FIG. 1 illustrates a block diagram of an exemplary endoscope system in accordance with one aspect of the invention.

The present invention relates generally to advantageous calibration techniques for blood content detection systems, e.g., optical blood content detection systems. These techniques facilitate calibration of blood content detectors usable in conjunction with endoscopes including traditional and in capsule-type endoscopes, as well as independently.

Referring to the drawings, like numbers indicate like parts throughout the views as used in the description herein, the meaning of "a," "an," and "the" includes plural reference unless the context clearly dictates otherwise. Also, as used in the description herein, the meaning of "in" includes both "in" and "on" unless the context clearly dictates otherwise. Also, as used in the description herein, the meanings of "and" and "or" include both the conjunctive and disjunctive and may be used interchangeably unless the context clearly dictates otherwise.

FIG. 1 depicts an exemplary block diagram 100 of a representative endoscope with blood content sensor components 1 to 6 and separate calibration component(s) 7. In particular, system 100 contains video monitor 1, observation light 2, endoscope image converter 3, blood content detector light 4, blood content measurement and calculation unit 5 and endoscope 6 with corresponding blood content sensor(s). Observation light source 2, and blood content detector light source 4 are connected to endoscope 6 and provide the respective light for general observation and blood content detection, respectively. Endoscope image converter 3 and blood content measurement and calibration unit 5 are similarly connected to endoscope 6 and may receive image and blood content data conveyed to a connected monitor 1.

A conventional scope, such as an endoscope or colonoscopy is usable for endoscope 6 in accordance with the invention. The particular type of scope used is not critical to practicing the invention. In operation, in scope observation mode, endoscope 6 is inserted or positioned proximate living tissue such as, for example, colon tissue or other tissue along the gastrointestinal tract. Observation light source 2 generates light that is transmitted via light conductors, such as optical fibers, (not shown) within endoscope 6 to illuminate the surface of a target region of living tissue. A portion of the illumination light interacts with the tissue under investigation and reenters endoscope 6 directly or through one or more lenses (not shown). This collected interacted light is processed by endoscope image converter 3 which may contain, for example, a CCD or other image processing device that creates analog or digital signals representing an image of the target tissue. The created image signals are provided by the image converter 3 to the monitor 1. The monitor 1 provides a video display based on the received signals to an operator or clinician.

However, unlike conventional endoscopes, the system 100 also advantageously includes components for blood content measurement. In determining the blood content measurement of a region of tissue, blood content light source 4 generates light that is conveyed through the endoscope 6. Endoscope 6, while contacting the tissue mucosa under investigation, illuminates a tissue region of interest with the light from blood content detector light source 4 and then detects a portion of the corresponding light that interacted with, for example, the mucosa or sub-mucosa of the illuminated tissue region.

Electrical signals based on the detected interacted light are produced by the blood content measurement and calculation unit 5. The interacted light is conveyed to the blood content measurement and calculation unit 5, such as for example, by an optical fiber. It should be noted, that due to the configuration of the series of lens and polarizers within the blood content sensor, the illumination light and portions of the interacted light are received by the optical fibers either horizontally or vertically aligned with respect to one another, i.e., substantially orthogonal to one another. This will be described in more detail with respect to FIG. 2.

The blood measurement and calculation unit 5 includes a data processor, that executes, for example, a data correction algorithms such as white correction represented in the following equation (1).

$$\Delta Ic(\lambda) = \frac{\Delta I(\lambda)}{\Delta Iw(\lambda)} = \frac{I_\Pi(\lambda) - I_\perp(\lambda)}{Iw_\Pi(\lambda) + Iw_\perp(\lambda)} \quad (1)$$

Where the symbols $\Pi$ and $\perp$ used in the numerator and denominator of equation (1) represent the spectrum of horizontally polarized light and the spectrum of vertically polarized light, respectively. In equation (1), $\lambda$ represents wavelength, $\Delta I(\lambda)$ indicates the measured difference polarization spectrum, $\Delta Iw(\lambda)$ is the spectrum measured using a standard white plate and is calculated by summing the white horizontal polarization spectrum $Iw\Pi(\lambda)$ and the white perpendicular polarization spectrum $Iw_\perp(\lambda)$, as shown in the denominator of equation (1). In the numerator of equation (1), the difference between the horizontal polarization spectrum $I\Pi(\lambda)$ and the perpendicular polarization spectrum $I_\perp(\lambda)$ is calculated and a signal indicative of $\Delta I(\lambda)$.

The blood measurement and calculation unit 5 calculates the blood content by using equation (2) below, which is shown in, for example, M. P. Siegel et al. "Assessment of blood supply in superficial tissue by polarization-gated elastic light-scattering spectroscopy," Applied Optics, Vol. 45, Issue 2, pp. 335-342 (2006), which is incorporated by reference herein.

$$\Delta I(\lambda) = \Delta I_{scattering}(\lambda) \exp[-\alpha A_{PG}(\lambda)] \quad (2)$$

Blood measurement and calculation unit 5, using a model equation, such as equation (2), provides a corresponding blood content indication or value to monitor 1 or other display devices. Alternatively, the blood measurement and calculation unit 5 may also provide the blood content value to a data validator (not shown) to perform a validation of such value. Blood measurement and calculation unit 5 may also provide the results from the detector to a comparator unit (not shown) to determine the validity of a measurement and to improve the accuracy of detection based on the measurement window.

Figure 2:
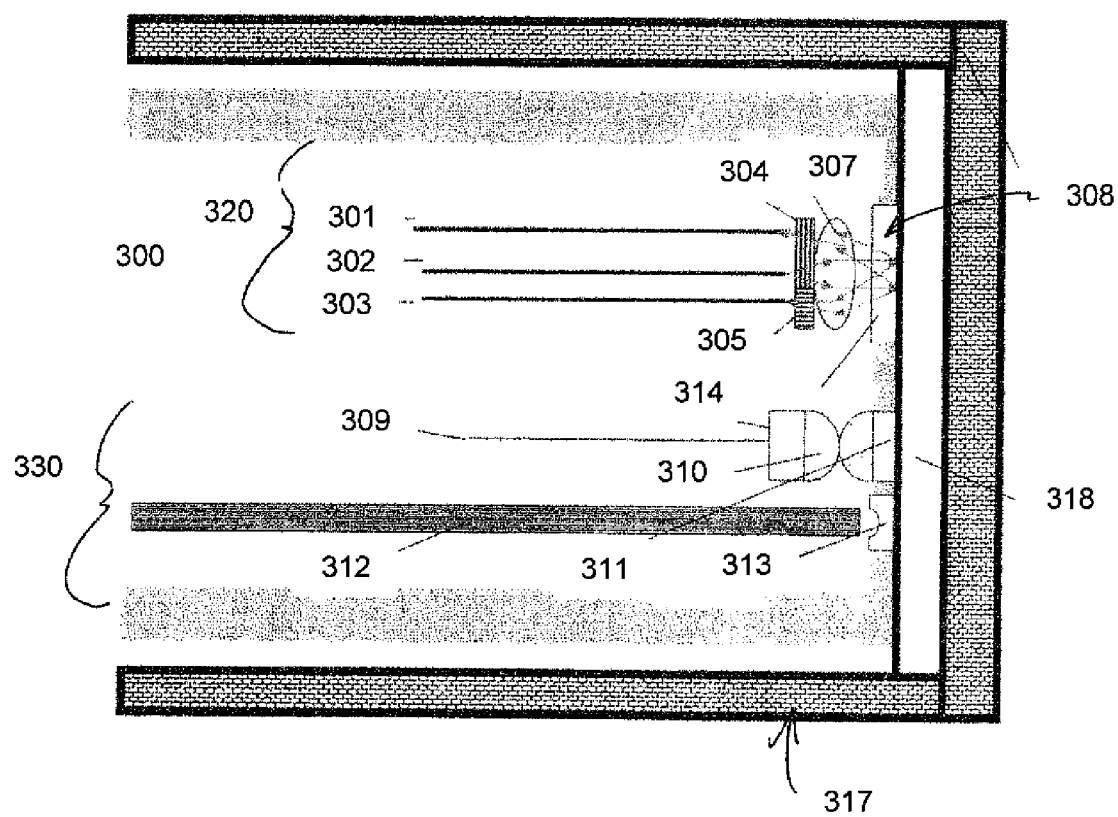
FIG. 2 illustrates an exemplary embodiment of a endoscope tip containing a blood content sensor in contact with a calibration device of the present invention.

Prior to collecting actual data, however it is imperative to calibrate the unit such that the amount of light reflected from and/or interacted with the illuminated tissue mucosa can be accurately measured for blood content detection. FIG. 2 depicts an embodiment of an endoscope system 300 in contact with a calibration reference device 317. Referring to FIG. 2, the endoscope tip of system 300 comprises a blood content detection section 320 and an optical observation section 330. The blood content detection section 320 contains receiving optical fibers 301 and 303, illuminator, such as illumination optical fiber 302, linear polarizers 304 and 305, lens 307, and blood content detection window 308. Observation section 330 contains an illuminator such as, light transmission optical fiber 312, illumination window 313, observation window 311, observation lens 310, imaging unit 314, such as a CCD or other imaging device, and transmission line 309.

Calibration reference device 317 may be in the form of a cap or other type of enclosure that is positionable or attachable in front of or fits over the tip of endoscope 7. The interior of calibration reference device 317, containing a reference target 318, is formed or coated with materials of a known or intended reference reflectivity. A suitable reference target 318 includes, for example, a white-colored diffuser panel such as a White Balance Reflectance Target available from Edmund Optics Inc., Barrington, N.J. (www.edmundoptics.com). The receiving optical fibers 301 and 303 may be coupled to the blood content measurement and control unit 5 of FIG. 1.

During calibration, light from the blood content detector source 4 in FIG. 1 is conveyed on illumination optical fiber 302 through polarizer 304 in FIG. 2. The emitted polarized or collimated light passes through lens 307 and blood content detection window 308. The emitted light strikes reference target 318 and a portion of such light is reflected and/or scattered. The calibration reference device 317 is configured such that light reflected from the reference target 318 at a predetermined angle or angles passes back through blood content window 308 and lens 307 at a predetermined angle or angles. Light passing through polarizer 304 is collimated and aligned in an angle of polarization with the transmitted light because it passed through the common polarizer 304. In the depicted embodiment, polarizer 305 is orthogonal to polarizer 304 and any light conveyed there to receiving optical fiber 303 represents collimated light with a different angle of polarization relative to the transmitted light. After entering the receiving optical fibers 301 and 303, the light is conveyed to blood content measurement and control unit 5 of FIG. 1.

$\Delta Iw(\lambda)$ of formula (1) denotes the spectrum intensity measured with respect to a reference target such as a white diffuser panel. In a similar manner, when living tissue is in contact with the blood content detector, $\Delta Iw(\lambda)$ represents the spectrum intensity measured from the living tissue. The intensity of the measured light can be corrected, i.e., calibrated in formula (1) by obtaining $\Delta Iw(\lambda)$ prior to collecting blood content tissue data.

Figure 4:
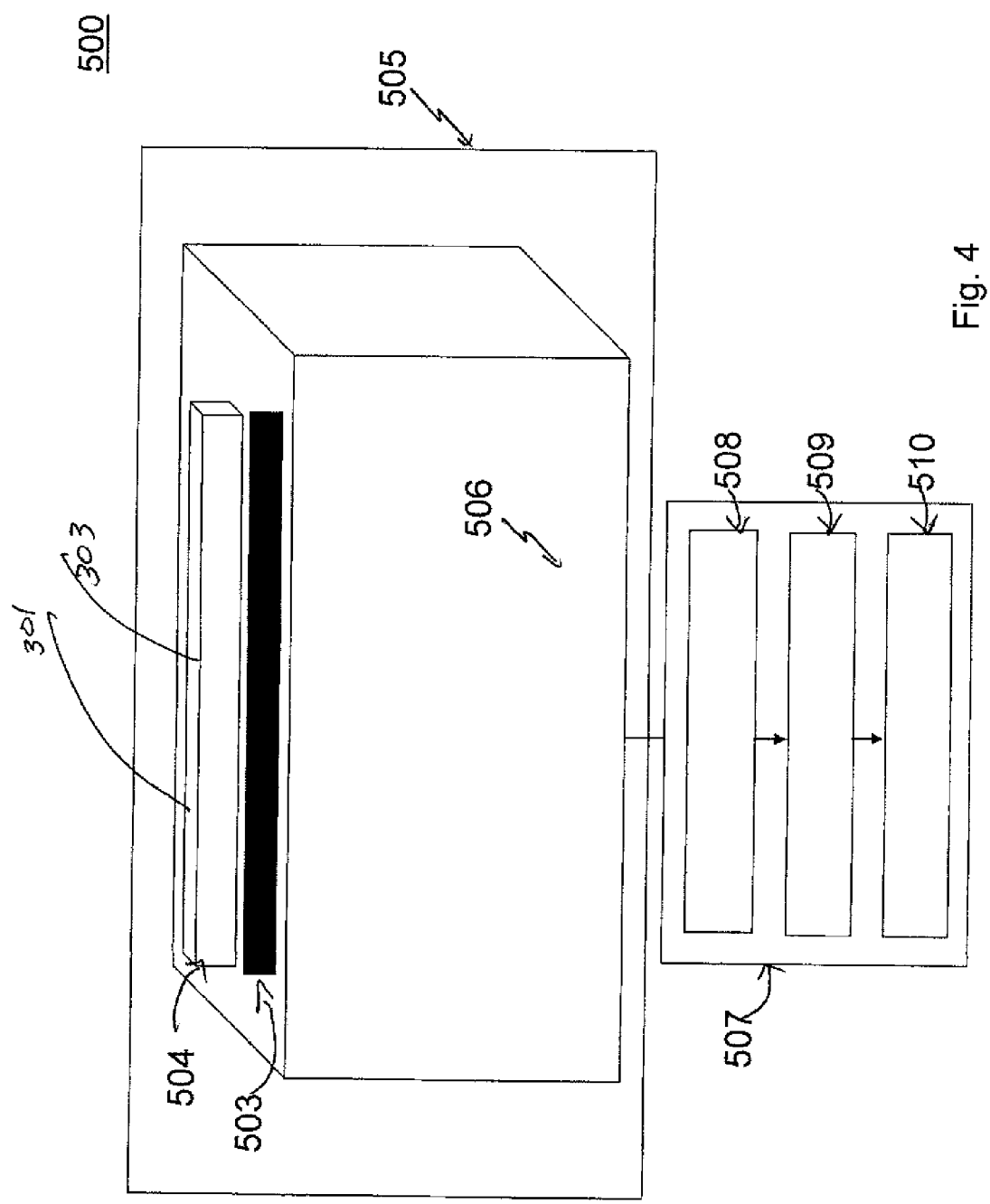
FIG. 4 illustrates a block diagram of the blood content detector measurement/calculation section of a device usable with the present invention.

An exemplary embodiment for wavelength calibration will now be described with respect to FIGS. 2 and 4. System 505 depicts the blood content measurement/calculation section of system 100 from FIG. 1. System 505 contains spectroscope 506 containing slit 503, optical filter 504, and calculation section 507. Calculation section 507 is comprised of wavelength calibration unit 508, intensity calibration unit 509 and blood content value unit 510. It should be noted, that optical filter 504 does not need to be located proximate to the spectroscope 506, but may be located at any point along the receiving fiber path, i.e., at either end of receiving fibers 301 and 303.

Figure 5:
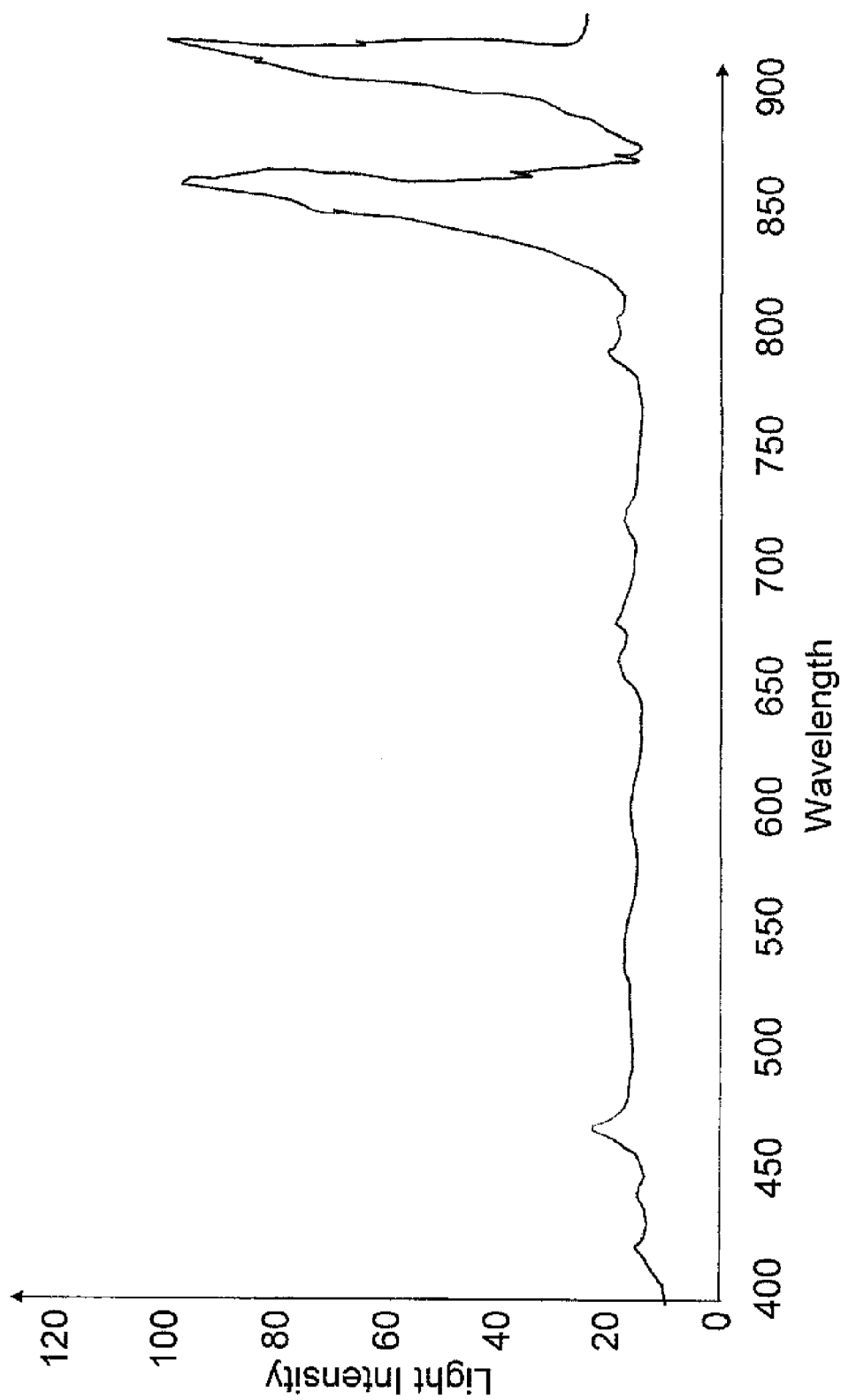
FIG. 5 illustrates an exemplary plot of the spectrum of light emitted from a light receiving fiber for use in accordance with an embodiment of the invention.

During a calibration procedure, the reflected light from diffuser panel 318 is conveyed to system 505 through light receiving fibers 301 and 303. Light receiving fibers 301 and 303, terminate at optical filter 504 in the present embodiment, and the conveyed light enters spectroscope 506 through slit 503. FIG. 5 depicts an exemplary optical spectrum of the light from receiving fibers 301 and 303 prior to passing through optical filter 504 with a white diffuser as the reference target 318.

Figure 6:
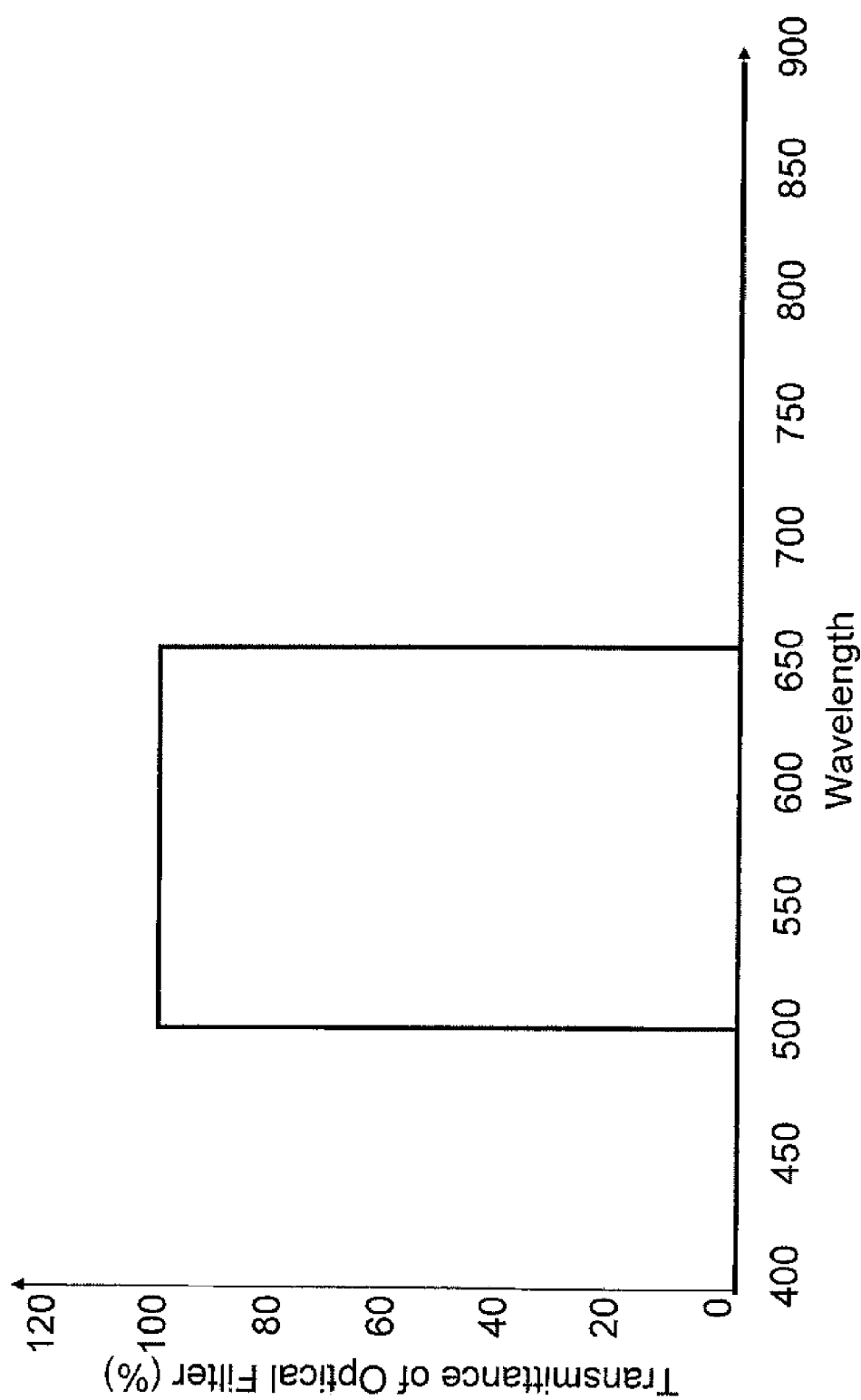
FIG. 6 illustrates an exemplary plot of transmittance vs. intensity of light in an exemplary blood content detection using an optical blood content detector.

FIG. 6, depicts the optical transmittance characteristics of an exemplary optical filter 504. As can be understood by FIG. 6, exemplary optical filter 504 is a band-pass filter that only allows the passage of a range of wavelengths required for blood content detection, for example, light in the 500 to 650 nm wavelength range. In this exemplary embodiment, utilizing filter 504 with the characteristics depicted in FIG. 6, only light in the 500 to 650 nm wavelength range will enter spectroscope 506 for processing.

In the wavelength calibration section 508, wavelength ranges characterized by a substantial fluctuation in intensity are detected. During wavelength calibration, detection of the wavelengths on the lower end of the spectrum, e.g., the lower end of the desired calibration optical filters range "X", 500 nm wavelength is assumed. Similarly, the wavelength on the upper end of the desired calibration spectrum, "Y", is, for example, 650 nm wavelength is assumed. In this embodiment, the wavelength $\lambda_{Zcor}$ determined by wavelength calibration correction at a given wavelength "Z" is corrected based on the following exemplary equation;

$$\lambda_{zcor} = X + \left(\frac{Z - X_{act}}{Y_{act} - X_{act}}\right) * (Y - X) \quad (3)$$

Where $X_{act}$ and $Y_{act}$ are the measured wavelengths corresponding to wavelengths "X" and "Y", and "Z" is the desired measurement wavelength, and $\lambda_{Zcor}$ is the corrected wavelength value of Z.

In accordance with equation (3), the use of optical filter 504 allows detection of wavelengths of fluctuating intensity across the wavelength range. Once these fluctuations are determined for wavelengths "X" and "Y," fluctuations for any given intermediate wavelength or wavelength range "Z" can be approximated, for example, by linear approximation. For example, using the above embodiment the calibration correction for a given wavelength "Z" falling between "X" and "Y" would be $$\lambda_Z = 500 + \left(\frac{Z - X_{act}}{Y_{act} - X_{act}}\right) * (650 - 500)$$

where $X_{act}$, and $Y_{act}$ are the measured low and high wavelengths in the range, respectively, and "Z" is the target wavelength. Once the wavelength fluctuations for specific wavelength ranges are known, calibration coefficients can be generated and applied to correct the intensity by intensity correction unit 509 in accordance with formula (1) and a corrected blood content value can be calculated by blood content unit 510 based on formula (2). Although an exemplary method for generating the spectral coefficients was described using linear approximation, it is likewise suitable to use other approximation methods for determining spectral coefficients in accordance with the invention including, for example, techniques normalizing detected intensity values across the desired spectrum between wavelengths X and Y.

In another exemplary embodiment, the system 300 disclosed in FIG. 2 may also be advantageously used to calibrate the white balance for use during observation mode. The optical observation section 330 may advantageously be calibrated in conjunction with blood content calibration, by utilizing the same reference target diffuser panel 318 and thereby reducing the number of reference targets and advantageously reducing costs. However, in this embodiment, it is important to not perform both calibrations simultaneously, because the stray light emitted from the light source for calibrating the observation components through window 313 may enter blood content window 308 thereby interfering with the blood content calibration procedure. To overcome this potential problem, the system 300 can be configured in such a way that the illumination light for optical observation emitted from 313 is automatically turned off or disabled during a time period during blood content detector calibration.

Figure 7:
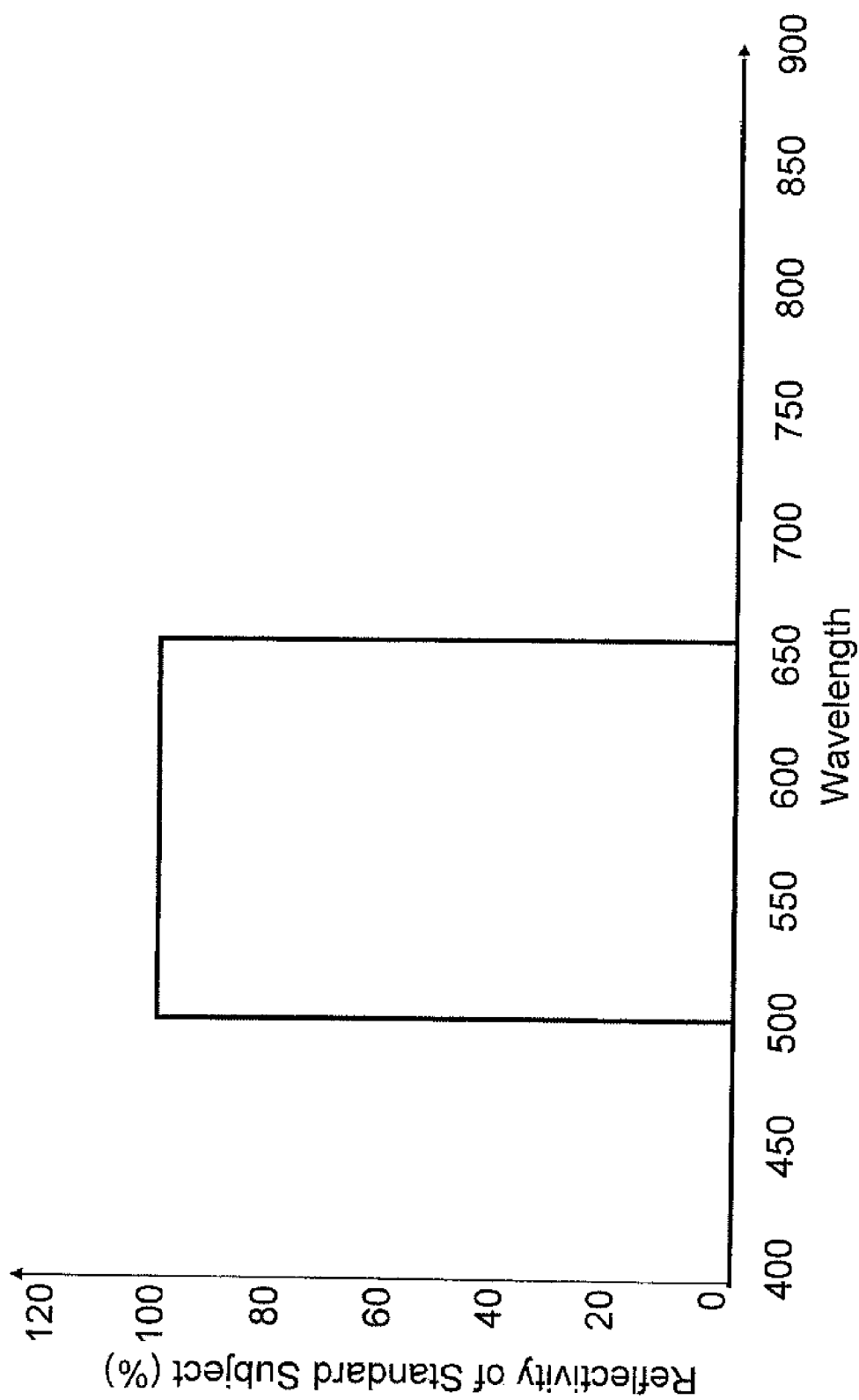
FIG. 7 illustrates an exemplary plot of reflectivity vs. intensity of light usable for calibration in accordance with the invention.

In another exemplary embodiment, a colored or shaded reference target is used in place of a white diffuser panel 318 as part of the calibration device 317 of FIG. 2. By relying on a colored or shaded reference target, the advantages of utilizing optical filter 504 may be realized without the actual use of such optical filter. A reference target 318, such as depicted in FIG. 2, may be directly tinted with a colored pigment, or a transparent film or optical filter may be placed adjacent a reference target to achieve the desired color or shading. In each case, the spectral transmittance of the reflected light from the reference target can be specified based on the spectral reflectivity of the altered or selected reference target. In this way, as depicted in FIG. 7, light in the wavelength range of interest, e.g., 500 to 650 nm range, will be conveyed to spectroscope 506 of FIG. 4 for calibration processing. Utilizing this embodiment, optical filter 504 of FIG. 4, is eliminated from the system, and spectroscope 506 may be used for measurement of systems with different wavelengths without having to modify spectroscope 506.

In another advantageous embodiment, the blood content detector light source 3 contains additional light sources, such as LEDs, or otherwise for emitting light in specific reference wavelength ranges for calibration purposes. In this embodiment, blood content detector light source 3 of FIG. 1 may contain a first LED that emits light wavelengths of greater intensity at the lower range of the visible light spectrum of interest, for example, the first LED may be a blue LED having a greater intensity at substantially the 500 nm wavelength range. Further, blood content detector light source 3, also may contain a second LED that emits greater light intensity at the upper end of the visible spectrum of interest, i.e., a red LED having greater intensity at substantially the 650 nm wavelength range. By utilizing these additional LEDs there is no need to filter the reflected light through an optical filter nor is there a need to provide a colored or tinted reference target. By utilizing such an advantageous embodiment, resource savings are realized.

Figure 8:
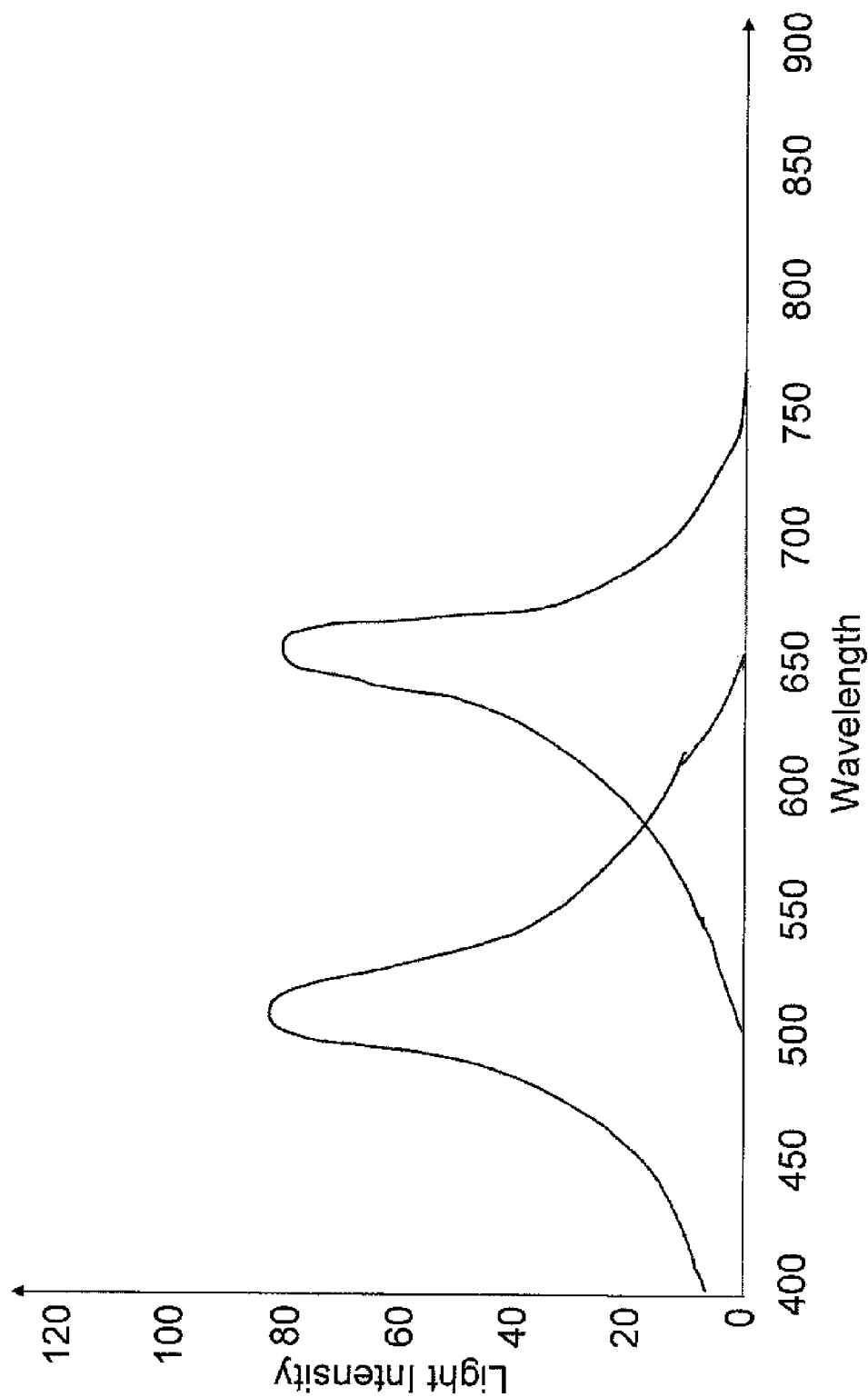
FIG. 8 illustrates an exemplary illumination spectrum as a result of calibration in accordance with the invention.

During calibration, as seen by the spectrum in FIG. 8, the two calibration LEDs are energized and emit superimposed light in their respective wavelength ranges via transmission optical fiber 302 striking a reference target such as a white diffuser panel 318. As discussed previously, wavelength calibration unit 508 can detect upper and lower transmission wavelength lines, i.e., 500 and 650 nm respectively, and performs the calibration calculation and blood content detection in accordance with equations 1-3.

As will be appreciated by one skilled in the art, the present invention is not limited to an endoscope system where the blood content detector is located at the tip or front of the endoscope as depicted in FIG. 2. The present invention is equally applicable to other endoscope configurations, e.g., such as where the blood content detector window is located on the circumference of the endoscope or within a corresponding colonoscope sheath. In the alternative, such calibration techniques are also useful for blood content detectors used within corresponding probes or on other independent structures.

Figure 3:
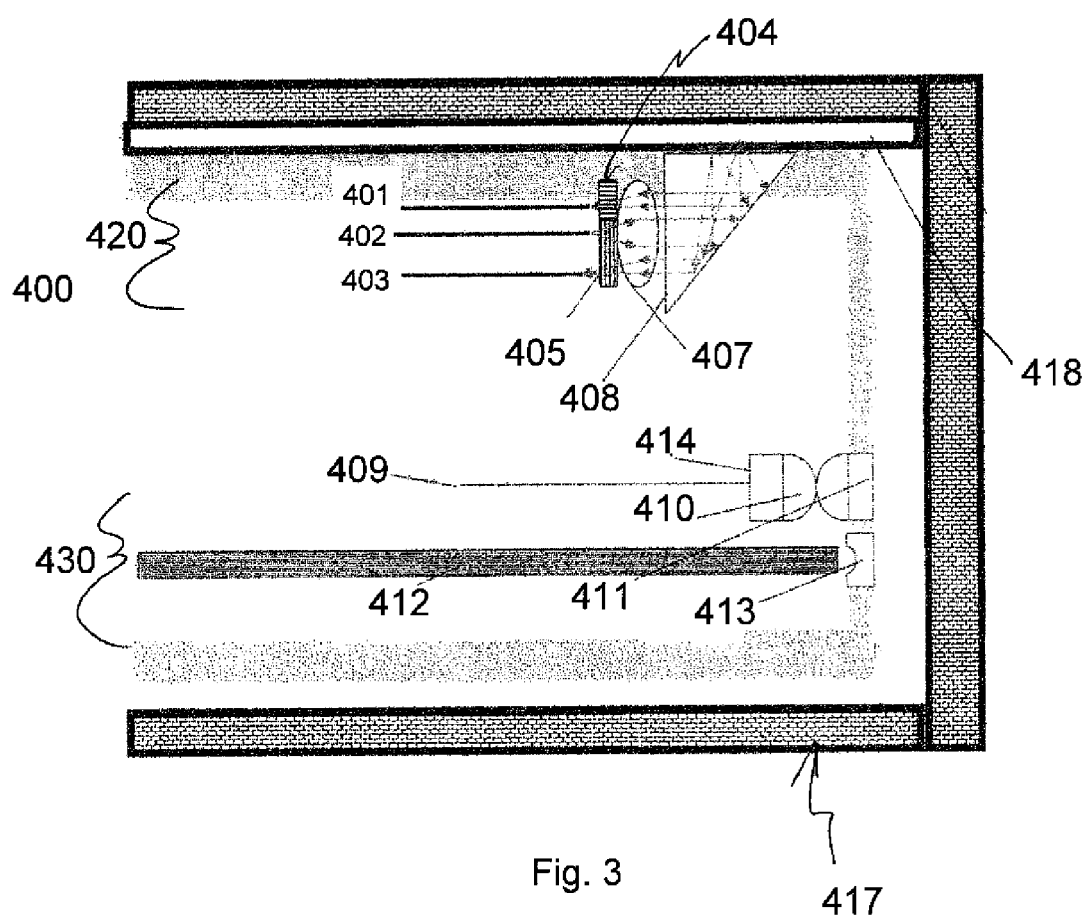
FIG. 3 illustrates a cross sectional view of an exemplary endoscope tip containing a blood content detector located on the circumference of the probe for calibration in accordance with the present invention.

In FIG. 3, endoscope system 400 is depicted in contact with a calibration reference device 417. Endoscope system 400 comprises a blood content detection section 420 and an optical observation section 430. The blood content sensor section 420 contains receiving optical fibers 401 and 403, illumination optical fiber 402, linear polarizers 404 and 405, lens 407 and prism 408 which in addition to bending the reflected and transmitted light at an angle acts as the blood content detection window. Receiving fibers 401 and 403 as well as illumination optical fiber 402 contact polarizers 404 and 405 for conveying and receiving optical signals. Lens 407 and prism 408 are aligned such that the emitted and received light are conveyed to and received from reference target 418.

Observation section 430 contains light transmission optical fiber 412, illumination window 413, observation window 411, observation lens 410, imaging unit 414, such as a CCD or other imaging device, and transmission line 409. Optical fiber 412 is in contact with illumination window 413 and conveys light from observation light source 2 of FIG. 1. Observation window 411 is aligned with observation lens 410 in such a way as to convey images to imaging unit 414. Imaging unit 414 is connected to transmission line 409 and conveys the image signals to endoscope image converter 3 of FIG. 1. Calibration reference device 417 may be a cap or other type of enclosure that fits over or contacts endoscope system 400. Lining the interior of 417 is reference target 418, which may be a white, colored or pigmented diffuser panel in accordance with the present invention.

During calibration of system 400 in FIG. 3, prism 408 contacts reference target 418. Light is emitted from illuminator optical fiber 402 and is conveyed through polarizer 404, lens 407 and prism 408 before being emitted onto reference target 418. The reflected light passes back through prism 408, lens 407 and polarizers 404 and 405. The interacted light is conveyed on receiving optical fibers 401 and 403 and calibration is performed in accordance with an embodiment of the present invention.

Figure 9:
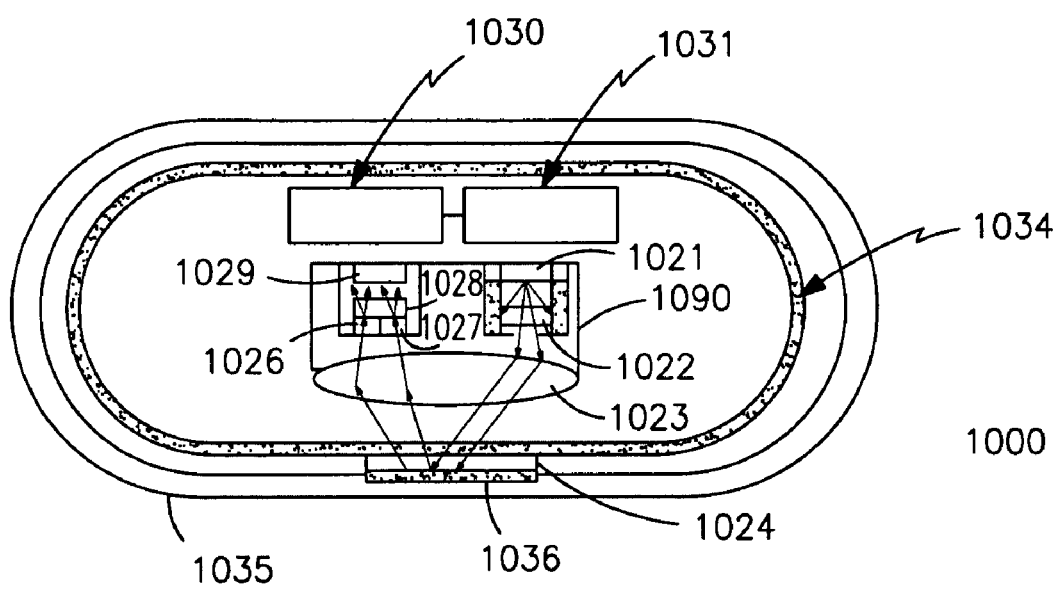
FIG. 9 illustrates a cross sectional view of an exemplary capsule type endoscope containing a blood content detector for calibration in accordance with the present invention.

Further, it will be appreciated by those skilled in the art, that the present calibration techniques are not limited to traditional endoscopes, but are equally applicable to capsule type endoscopes as well. As depicted in FIG. 9, blood content detector capsule endoscope system 1000 contains three main components. Within capsule shell 1034, is located (1) a power supply 1030 for generating DC power to the other components of the capsule; (2) data transmitter 1031 for transmitting the blood content data to a host processing unit (not shown); and, (3) a blood content sensor portion 1090. The blood content sensor portion 1090 may be comprised of, for example, light source 1021, typically a LED or other suitable light source, a linear polarizer 1022, lens 1023, blood content window 1024, linear polarizer 1026, linear polarizer 1027, transmissive grating 1028 and linear sensor 1029.

To facilitate calibration of the blood content sensor capsule prior to ingestion or insertion into a body cavity, any one of the advantageous techniques described herein, may be utilized. As depicted in FIG. 9, capsule shell 1034, is surrounded by a protective membrane 1035 that contains a reference target 1036. Reference target 1036 is positioned in contact with blood content sensor window 1024, in order to provide a reference target surface for use during the calibration procedure. Reference target 1036 may be a calibration reference device such as a white diffuser panel or a tinted standard depending on the method of calibration.

As with traditional endoscopes, light source 1021 is energized and light passes through polarizer 1022, lens 1023, and blood content sensor window 1024. The emitted light strikes reference target 1036 and is reflected back though window 1024, lens 1023, and polarizers 1026 and 1027. The received reflected light passes through transmissive grating 1028 and is conveyed to linear sensor 1029. The data from linear sensor 1029, or other optical sensing device, is transmitted by any known means via data transmitter 1031, and calibration factors or coefficients are calculated in accordance with any of the above embodiments. In this manner, the capsule may be calibrated before it is inserted into a body cavity ensuring accuracy in the data gathered.

The placement of reference target 1036, is not limited to the inside of protective membrane 1035, but may be located in other configurations, such as a reusable enclosure, or other holding fixture, as long as the sensor window 1024 is able to contact standard subject 1036, and the window 1024 is shielded from extraneous light.

Figure 10:
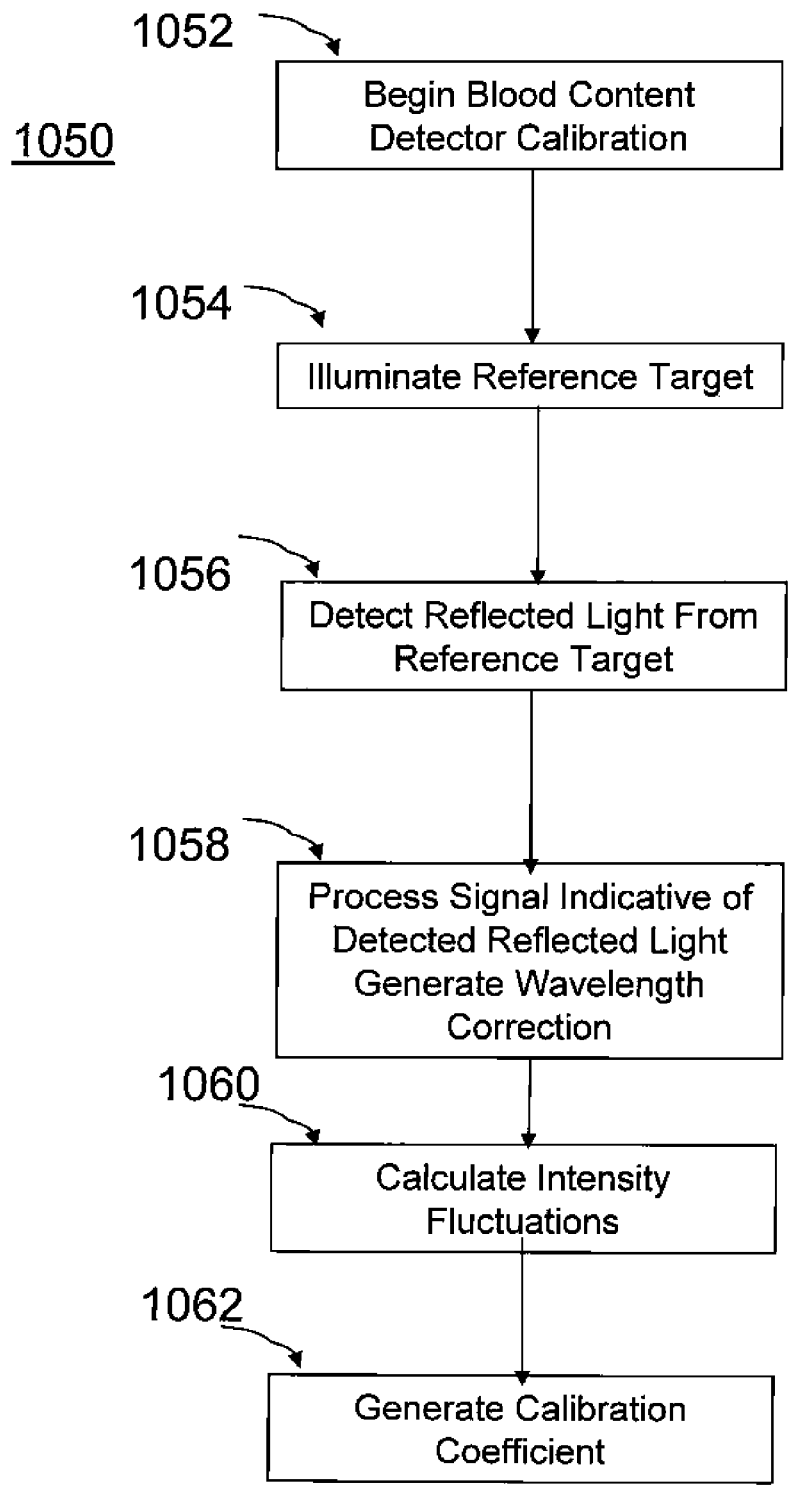
FIG. 10 is a flow diagram of an exemplary calibration procedure in accordance with the present invention.

FIG. 10 shows a flow diagram 1050 of the representative steps for calibrating blood content sensors in accordance with the invention. The exemplary steps of the diagram 1050 will now be described with regard to the components illustrated in FIGS. 1, 2, and 5. However, it should be readily understood that other components and system configurations are usable in carrying out the calibration process of the present invention. The user initiates the blood content calibration procedure in step 1052 by positioning the probe 6 of FIG. 1 proximate to the reference target 318 as illustrated in FIG. 2. Then in step 1054, the blood content light source 4 of FIG. 1, illuminates reference target 318 with light of a specific wavelength. In step 1056, the blood content measurement and calibration unit 505, shown in FIG. 5, detects the corresponding reflected light from the reference target 318. In step 1058, calculation section 507 of FIG. 5, processes the generated signal representing the detected reflected light utilizing wavelength calibration unit 508. In step 1060, intensity calibration unit 509 calibrates for intensity fluctuations, and in step 1062, blood content value unit 510 generates the calibration coefficients.

While the foregoing description and drawings represent the preferred embodiments of the present invention, it will be understood that various changes and modifications may be made without departing from the spirit and scope of the present invention. Although the blood content sensors used with the invention were described with respect to use with scopes, such as endoscopes or colonoscopes, it should be readily understood that the principles of the invention are equally applicable to blood content sensors employed alone or with other medical instruments.

What is claimed is:

1. A calibration method for a blood content detector of a medical device comprising the steps of:
   positioning said blood content detector of a medical device relative to a colored reference target;
   illuminating a region of the colored reference target with light of a specific wavelength range, the reference target reflecting light within at least a part of a wavelength range of 500 nm to 650 nm;
   said blood content detector detecting light reflected from the reference target;
   processing a signal from said blood content detector indicative of the detected light relative to a desired spectral characteristic for said specific wavelength range; and
   generating at least one calibration coefficient for said blood content detector based on the processed signal.

2. The method of claim 1 wherein the processing step includes comparing said signal to the desired spectral characteristic.

3. The method of claim 1 for calibrating a blood content detector located in a capsule type endoscope.

4. The method of claim 1 comprising the additional step of storing the calibration coefficients.

5. The calibration method of claim 1 wherein the calibration coefficient is based on a corrected wavelength.

6. The calibration method of claim 1 further comprising the steps of:
   determining at least one corrected wavelength based on the light reflected from the reference target,
   wherein said calibration coefficient is based on said corrected wavelength.

7. The method of claim 1 wherein positioning a medical device with a blood content detector for calibration further comprises the step of inserting said blood content detector of a medical device into an enclosure, said enclosure having a reference target fixed to the enclosure.

8. A calibration method for a blood content detector comprising the steps of:
   illuminating a region of a reference target with light from a first light source at a first specific wavelength range and light from a second light source at a specific second wavelength range;
   detecting the first and second light reflected from the reference target;
   processing a signal indicative of the detected reflected first and second light relative to desired spectral characteristics for said first and second specific wavelength ranges; and
   generating calibration coefficients based on the processed signals.

9. The method of claim 8 wherein the first light has a first substantially maximum intensity portion at a lower portion of a blood content detection wavelength range, and wherein the second light has a second substantially maximum intensity at an upper portion of the blood content detection wavelength range.

10. The method of claim 8 wherein the blood content detection wavelength range is 500 to 650 nm.

11. The calibration method of claim 5 further comprising the step of storing the calibration coefficients.

12. The calibration method of claim 5 wherein the calibration coefficient is based on a corrected wavelength.

13. The calibration method of claim 5 further comprising the steps of:
   determining at least one corrected wavelength based on the first and/or second light reflected from the reference target,
   wherein said calibration coefficient is based on said corrected wavelength.

14. A calibration method for an endoscope comprising a blood content sensor and an observation portion comprising the steps of:
   positioning said blood content detector and observation portion of the endoscope relative to a colored reference target;
   illuminating a region of the colored reference target with light from the observation portion, the reference target reflecting light within at least a part of a wavelength range of 500 nm to 650 nm;
   detecting the reflected light from the reference target;
   performing a white balance for the general observation portion based on the reflected light;
   disabling the light from the general observation portion,
   illuminating a region of the reference target with light of a specific wavelength range;
   said blood content detector detecting light reflected from the reference target;
   processing a signal indicative of the blood content detector detected light relative to a desired spectral characteristic for said specific wavelength range; and
   generating calibration coefficients based on the processed signal.

15. The calibration method of claim 14 further comprising the step of storing the calibration coefficients.

16. The calibration method of claim 14 wherein the calibration coefficient is based on a corrected wavelength.

17. The calibration method of claim 14 further comprising the steps of:
   determining at least one corrected wavelength based on the light reflected from the reference target,
   wherein said calibration coefficient is based on said corrected wavelength.

* * * * *